United States Patent
Boese et al.

(10) Patent No.: US 8,103,078 B2
(45) Date of Patent: Jan. 24, 2012

(54) METHOD FOR DETERMINING ECG-TRIGGERED RECORDING TIMES FOR IMAGING TO SUPPORT INTERVENTIONAL AND DIAGNOSTIC CARDIAC PROCEDURES

(75) Inventors: Jan Boese, Eckental (DE); Malte Meesmann, Veitshöchheim (DE)

(73) Assignee: Siemens Aktiengesellschaft, Munich (DE)

( * ) Notice: Subject to any disclaimer, the term of this patent is extended or adjusted under 35 U.S.C. 154(b) by 1029 days.

(21) Appl. No.: 12/012,160

(22) Filed: Jan. 31, 2008

(65) Prior Publication Data

US 2008/0187092 A1    Aug. 7, 2008

(30) Foreign Application Priority Data

Feb. 2, 2007  (DE) .......................... 10 2007 005 376

(51) Int. Cl.
*G06K 9/00*    (2006.01)
(52) U.S. Cl. .......................... 382/132; 378/95
(58) Field of Classification Search ................ 378/8, 95; 382/128, 131, 132; 600/428
See application file for complete search history.

(56) References Cited

U.S. PATENT DOCUMENTS

| 4,878,115 A | 10/1989 | Elion |
| 2008/0039719 A1* | 2/2008 | Boese et al. .................. 600/428 |

FOREIGN PATENT DOCUMENTS

| DE | 102 14 763 A1 | 10/2003 |
| DE | 102 47 299 A1 | 4/2004 |
| DE | 10 2004 057 308 A1 | 7/2006 |
| DE | 10 2005 027 944 A1 | 1/2007 |

* cited by examiner

*Primary Examiner* — Jurie Yun

(57) ABSTRACT

The invention is directed to a method for determining a plurality of ECG-triggered recording times for cardiac imaging, comprising the steps: recording a plurality of images of the heart at predetermined time intervals; assigning the images to specific cardiac phase times; comparing the images in order to determine similarity measures between two images in each case, said similarity measures representing states of the heart requiring to be imaged that are similar in terms of imaging technology; identifying a group of images with mutual similarity measures in a predefined area, between the pairs of images; and specifying the cardiac phase times associated with the images in the group as the plurality of ECG-triggered recording times. In a further aspect the method can additionally include the step of performing the moving-target imaging based on image recordings at the specific recording times with the aid of ECG triggering.

19 Claims, 1 Drawing Sheet

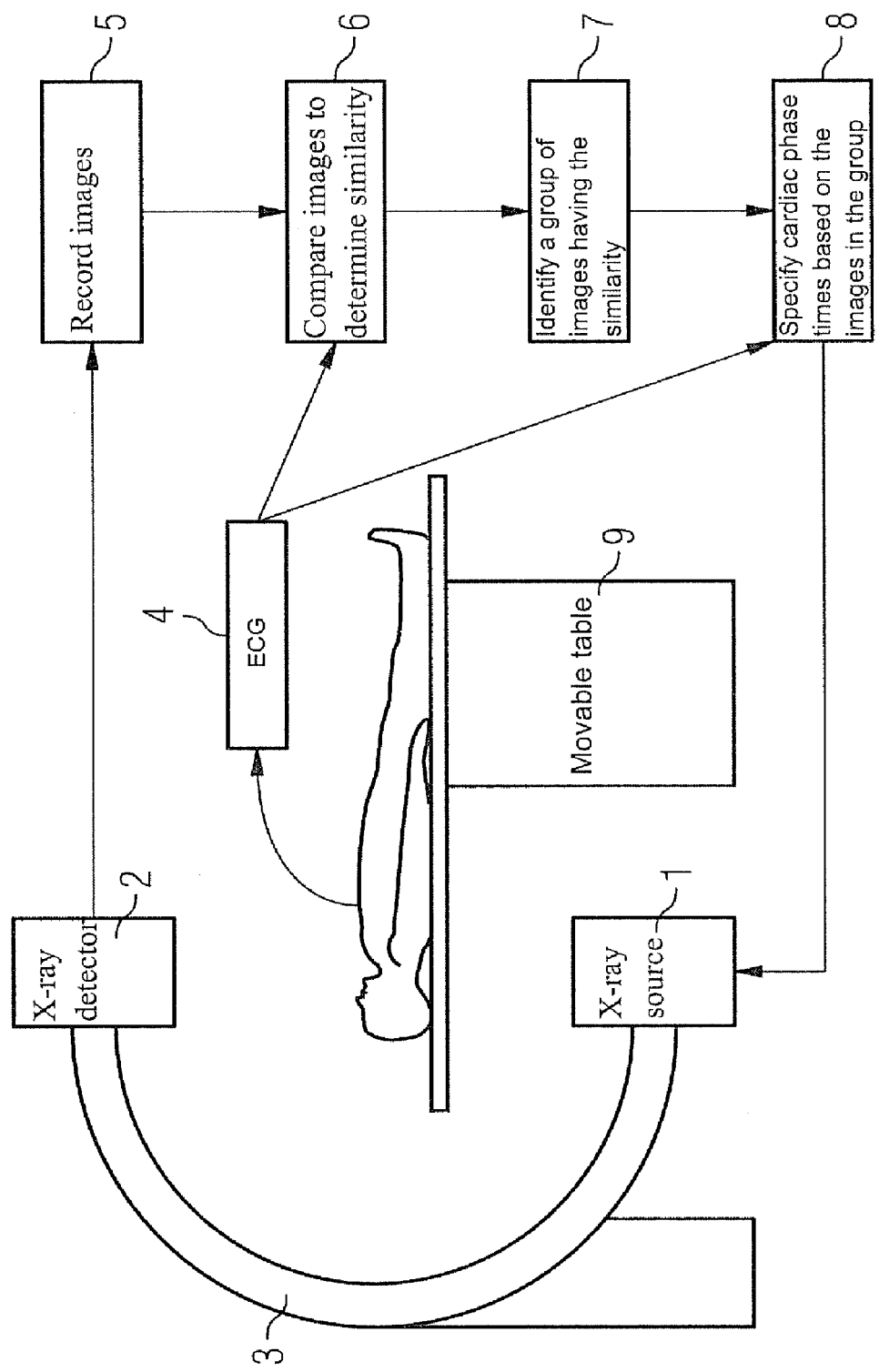

METHOD FOR DETERMINING ECG-TRIGGERED RECORDING TIMES FOR IMAGING TO SUPPORT INTERVENTIONAL AND DIAGNOSTIC CARDIAC PROCEDURES

CROSS REFERENCE TO RELATED APPLICATIONS

This application claims priority of German application No. 10 2007 005 376.4 filed Feb. 2, 2007, which is incorporated by reference herein in its entirety.

FIELD OF THE INVENTION

The invention is directed to a method for determining ECG-triggered recording times for imaging as well as to a method for moving-target cardiac imaging and includes in particular methods and systems for supporting interventional and diagnostic cardiac procedures.

BACKGROUND OF THE INVENTION

In the prior art, X-ray systems are mostly used for supporting interventional or diagnostic procedures on the heart or in the region of the heart, in particular for visualizing the instruments used. In this context the term "fluoroscopy" (radioscopy) refers to the recording of series of X-ray images which are displayed directly during the recording in real time, on a computer screen for example, and are intended to assist the operator or examiner in ensuring the correct positioning and movement of the instruments.

A problem with prior art fluoroscopy is that patient and operating staff are exposed to radiation. The standard image rate of 15 images per second obviously means that 15 X-ray irradiations are also performed per second, which, in the case of relatively long interventions in particular, constitutes a substantial radiation load for the patient and also, due to the necessary movements and inadequate X-ray protection associated therewith, for the examiner and the support staff, even when modern, sensitive X-ray devices are used. For this reason methods of minimizing the exposure to radiation have been sought since the introduction of fluoroscopy. A simple approach to reducing the exposure to radiation is to reduce the image rate. Thus, for example, compared with a standard image rate of 15 images per second, reducing the image rate to 3 images per second can reduce the exposure to radiation by a factor of five. However, an approach of this kind revealed itself as problematic, since the heart moves a great deal during the relatively long interval between the images and in addition the images occur in random cardiac phases, with the result that the series of images recorded sequentially in time becomes unstable and the image jerks more or less arbitrarily.

To overcome this problem it has been proposed to perform an ECG-triggered fluoroscopy in which the current cardiac phase is derived from the patient's ECG signal and only one fluoroscopy image per heartbeat is recorded. Typically, the R wave of the ECG signal is detected for this purpose and an image is recorded immediately after the R wave or after a selectable delay relative to the current R-R interval (for example at 30%). At a typical heart rate of between 60 and 80 beats per minute, this therefore results in approx. 1 to 1.3 images per second. The proposed method at least has the advantage that the images always originate from the same cardiac phase and therefore the image sequence is rendered considerably more stable. A significant problem with ECG-triggered fluoroscopy; however, is that the image rate, at approx. 1 image per second, is very low. A rapid movement of instruments, such as for example when advancing a guide wire, is practically impossible to control and monitor using this technology.

For this reason, finally, it has likewise been proposed in the prior art to record a plurality of images per heart cycle during ECG-triggered fluoroscopy. Thus, it is conceivable for example to record an image at the start and an image in the middle of the R-R interval. In this way the image rate can be increased to approx. 2 images per second.

With this approach, however, there is once again the problem that the two images may not necessarily originate from optically similar cardiac phases.

In addition there is the problem in practice of finding fixed trigger times, since the progression of the heart movement is influenced by many parameters, including, inter alia, the local position of the instrument in the heart, the angulation, the current heart rate, the individual pump function of the heart, and the individual anatomy.

SUMMARY OF THE INVENTION

It is therefore the object of the present invention to find an approach with the aid of which it is possible to obtain a consistently usable and clearly distinguishable cardiac image while nonetheless ensuring low exposure to radiation.

This object is achieved by the method for determining a plurality of ECG-triggered recording times as well as by the method for moving-target cardiac imaging as claimed in the independent claims. Further advantageous embodiments, details and aspects of the present invention can be found in the dependent claims, the description and the accompanying drawing.

The basic idea of the invention is to "learn", i.e. determine in advance, the optimal trigger times before switching to ECG-triggered fluoroscopy comprising a plurality of image recordings per heart cycle. For this reason an untriggered image recording phase is linked to an analysis for the purpose of determining optimal recording times.

Accordingly, the invention is initially directed to a method for determining a plurality of ECG-triggered recording times for imaging on a heart requiring to be imaged, which method comprises the steps:

recording a plurality of images of the heart at predetermined time intervals;

assigning the images to specific cardiac phase times;

comparing the images in order to determine similarity measures between two images in each case, said similarity measures representing states of the heart requiring to be imaged that are similar in terms of imaging technology;

identifying a group of images with mutual similarity measures in a predefined area, between the pairs of images; and specifying the cardiac phase times associated with the images in the group as the plurality of ECG-triggered recording times.

In this context, ECG triggering, as also known in the prior art, is understood to mean initiating the recording of an image when a specific cardiac phase determined by means of a cardiogram technology has been reached. The recording time is the instant in time, relative to the cardiac activity, at which an image is to be recorded by means of the imaging method used (typically X-ray radiography). Imaging is understood to mean the provisioning of images of the heart by means of a specific recording method.

An image signifies an image acquisition that is to be performed during a single triggering event. A cardiac phase time is understood to mean an instant in time within the cardiac phase. A similarity measure, in the context of the present invention, is a numeric value or a group of numeric values which indicates the similarity between two compared images specified in accordance with specific criteria.

The method according to the invention identifies a group of images with mutual similarity measures. The group of images is therefore determined from the underlying values for the similarity measures, which values are intended to lie in a predefined range. The similarity measure quantifies the degree of correspondence between the two images. Useful similarity measures are, for example, cross-correlation or "mutual information".

The information thus obtained can then be stored in a matrix whose fields are the similarity measures of the individual comparison pairs.

The method according to the invention results in the specification of a number of cardiac phase times (relative, for example, to an arbitrarily selectable start time of the cardiac phase) which are similar to one another to a predefined (usually maximally high) degree and which, when successively displayed on the screen, produce an optimally stable image. The principle of identifying optimally matching images within a cardiac phase or over a plurality of cardiac phases using a normal recording speed thus enables advantageous use of the associated times in the cardiac phase for producing ECG-triggered image recordings during the actual examination or surgical intervention.

In a preferred embodiment, the identified plurality of images is a greatest plurality of images for which the mutual similarity measure exceeds a predefined value. By specifying the minimum similarity measure to be complied with it is possible to control the desired symmetry of the impression of the image appreciation of the image recordings generated thereafter, albeit at the cost that, with an increased similarity measure, the number of possible images still falling below the similarity measure drops, with the result that potentially, if the images are too similar, there is no longer a sufficient number of image recordings available to guarantee a usably rapid successional flow of the images. For this reason the number of image recordings per heart cycle that must be determined as a minimum can also be specified as an additional condition and the similarity measure can be adapted thereto. It is clear that the two quantities vary and can also be handled automatically by the system that performs the method.

The cardiac phase times for the ECG triggering can now be determined by means of an ECG as is usual for patient monitoring in the prior art. Alternatively it is also possible to use an ICG (induction cardiogram), which delivers a different cardiogram pattern, but can nonetheless also be regarded as informative in terms of the progression of cardiac activity.

The comparison of the individual image recordings can be carried out within one heart cycle or with image recordings that have been obtained over a plurality of heart cycles. Thus, a comparison takes place either within the individual image recordings of each heart cycle that has been acquired, or across cycle boundaries.

If a patient on whose heart the method is carried out is lying on a movable table, the table movements can preferably be recorded and compensated for when making the comparison of the images. In this case, either the images can be corrected according to the mechanically measured table displacement or (optionally also in addition) image-based registration methods are used in order to remove two-dimensional translation movements of the heart due to table displacement before the similarity measures are calculated.

In a preferred embodiment the similarity measure for respective pairs of images is determined, not in the complete image, but in predefined areas of the image which can be defined automatically or manually. This can be accomplished for example by coordination onto a relatively small image section.

Furthermore, prior to carrying out the comparison and/or specifying the areas to be compared, image processing functions can be performed in order to highlight certain features and thereby simplify the determining of the similarity measure. In this case, the features related to the action of the heart in particular can be accentuated by the image processing. In the case of fluoroscopy images, for example, filters can be used which emphasize the instruments (e.g. guide wires) and suppress the background. Other image processing steps, such as for example histogram equalization, are helpful in eliminating influences that are not related to heart movement.

In a further aspect the invention is directed to a method for moving-target cardiac imaging which includes the above-described aspect of determining ECG-triggered recording times. The method comprises the following steps:

determining a plurality of ECG-triggered recording times according to the inventive determination method; and performing the moving-target imaging based on image recordings at the specific recording times with the aid of ECG triggering.

Within the scope of the invention, ECG triggering is understood in this context to mean triggering by means of an ECG or by means of an ICG.

When moving-target imaging is performed, the image recordings produced are preferably compared with one another continuously or at specific time intervals again in terms of the currently present similarity measure. In this way, for example, changes in the patient's position which would reduce the similarity measures of the recording times used can be detected and subsequently corrected by means of suitable countermeasures.

If the similarity measure falls below a threshold value during such a repeated determination, the recording time affected thereby is preferably varied until the similarity measure once again lies above the threshold value. In this way it is possible, during the course of the ECG-triggered imaging and without repeated non-triggered image recording sequences, to adapt the imaging to changing environments or conditions.

The method can also be configured in such a way that it can be restarted by a user input, for example if the examiner or operator realizes that the image quality or image steadiness of the generated image recordings has deteriorated.

As a further variant of the method according to the invention it can be provided that the step of determining the recording times is repeated in the event of changes in the heart rate, which can, of course, also be determined by the ECG measurement.

Finally, in a further preferred embodiment, the number of recording times actually used for imaging from the group of recording times can be determined as a function of the heart rate such that the resulting image rate remains essentially constant in the event of changes in the heart rate. This method likewise implies the possibility of using only a subset from the group of identified cardiac phase moments with optimum similarity for the actual imaging, which can also be used to minimize the exposure to radiation during the execution of the method according to the invention.

BRIEF DESCRIPTION OF THE DRAWINGS

The invention will be explained below with the aid of a more tangible exemplary embodiment in which reference is made to the accompanying FIGURE, which schematically represents a measuring arrangement including the necessary method steps for the method according to the invention.

DETAILED DESCRIPTION OF THE INVENTION

The method according to the invention has several phases. Initially, the fluoroscopy starts in a special organ program for ECG-triggered fluoroscopy in a non-triggered mode. Following online evaluation of several seconds of image recording in the background, the system then switches automatically into the ECG-triggered mode. Alternatively, if an angiography image was recorded beforehand, this preliminary run can be dispensed with entirely and instead, when ECG-triggered fluoroscopy is selected, a previously recorded or optionally an angiography scene of the patient lying on a movable table 9 that matches in respect of the angulation can be evaluated. The system thus operates as follows: In phase 1, images are recorded in a non-ECG-triggered mode with the aid of an X-ray source 1 and a detector 2 of the C-arm angiography system 3 shown in the left half of FIG. 1. In this case the images can be either those recorded in the first seconds of a fluoroscopy image recording session, as represented by the image recording step 5 in FIG. 1, or alternatively angiography acquisitions that were generated previously, for example.

The images acquired during this image recording session are supplied, preferably online, i.e. while recording is still taking place, to a preprocessing step in which the present image series and the associated signals recorded by the ECG 4 are used to determine the times that are optimal in the case of multiple triggering. Specifically, the following substeps are carried out.

First, each recorded image is assigned a cardiac phase. This can be defined for example in % of the R-R cycle (0 to 100%) or alternatively as a time lag in milliseconds after the R wave, in which case the latter approach cannot effectively compensate for changes in heart rhythm, but reduces the evaluation overhead.

Next, each image of a specific heart cycle is compared with every other image within this same heart cycle (comparisons over a plurality of heart cycles also being possible), in which a similarity measure is determined (step 6 in FIG. 1). This results in a matrix containing similarity measures which is processed further in step 7. The similarity measure quantifies the degree of correspondence between the two images. Useful similarity measures are, for example, cross-correlation or what is termed "mutual information".

From the associated cardiac phases a group of N cardiac phases is now identified in step 7, the associated images of which are not only distributed as homogeneously as possible over the R-R cycle, but also have the highest possible similarity to one another. In this case N is the number of trigger times per heart cycle, i.e. the number of elements in the specific group. By means of a weighting factor it can be defined whether the selection is to be more dependent on the similarity criterion or on the homogeneity criterion.

In phase 2, the cardiac phase times found are used as trigger times for ECG-triggered fluoroscopy and are used in step 8 for image recording using the X-ray source.

In an optional subsequent phase 3, the previously determined optimal parameters, i.e. recording times, can be reset either manually or automatically. The latter can be effected for example in the event of a change in heart rate or angulation.

In spite of the enormous potential for dosage reductions, ECG-triggered fluoroscopy is hardly used today in routine examinations. The reason for this is that the image rate, averaging one image per heart cycle, is frequently felt to be too low.

The present invention solves the problem of low image rate by optimized multiple ECG triggering, thereby making the method of ECG-triggered image recording routinely usable as an effective technique for the first time.

With two, three or more time-optimized pulses per heartbeat, the X-ray dose can be reduced by a factor of up to five compared to normal fluoroscopy at 15 images per second. As a result of suppressing the movement of the heart when the heart is displayed on a monitoring screen, a stable image impression is produced in addition.

The invention claimed is:

1. A method for determining a plurality of ECG-triggered recording times for a cardiac imaging recording of a patient, comprising:
    recording a plurality of images of a heart of the patient;
    assigning the images to specific cardiac phase times;
    comparing the images for determining a similarity measure;
    identifying a group of images having the similarity measure in a predefined area; and
    specifying the cardiac phase times associated with the images in the group as the ECG-triggered recording times to be used in the cardiac imaging recording.

2. The method as claimed in claim 1, wherein the images are recorded at predetermined time intervals.

3. The method as claimed in claim 1, wherein the images in the group comprise the similarity measure in a predefined area of the images.

4. The method as claimed in claim 1, wherein the similarity measure represents a state of the heart that is similar in terms of imaging technology.

5. The method as claimed in claim 1, wherein a largest number of images having the similarity measure that exceeds a predefined value are identified in the group.

6. The method as claimed in claim 1, wherein the cardiac phase times are determined by an ECG.

7. The method as claimed in claim 1, wherein the cardiac phase times are determined by an ICG.

8. The method as claimed in claim 1, wherein the images recorded within one heart cycle are compared.

9. The method as claimed in claim 1, wherein the images recorded within a plurality of heart cycles are compared.

10. The method as claimed in claim 1, wherein movements of a patient table on which the patient lies are recorded and compensated for when comparing the images.

11. The method as claimed in claim 1, wherein the images are compared in a previously specified area of the images.

12. The method as claimed in claim 1, wherein image processing aimed at highlighting a certain feature of the images is performed before making a comparison or specifying an area to be compared.

13. A method for performing a moving-target cardiac imaging of a patient, comprising:
    recording a plurality of images of a heart of the patient;
    assigning the images to specific cardiac phase times;
    comparing the images for determining a similarity measure;
    identifying a group of images having the similarity measure;
    specifying the cardiac phase times associated with the images in the group as an ECG-triggered recording times; and performing the moving-target imaging based on image recordings recorded at the ECG-triggered recording times.

14. The method as claimed in claim 13, wherein the image recordings are compared with one another continuously or at specific time intervals based on a currently present similarity measure.

15. The method as claimed in claim 13, wherein the ECG-triggered recording times are determined based on the similarity measure that is above a threshold value.

16. The method as claimed in claim 13, wherein the method is restarted by a user input.

17. The method as claimed in claim 13, wherein the ECG-triggered recording times are repeatedly determined with a change of a heart rate of the patient.

18. The method as claimed in claim 13, wherein a subset of ECG-triggered recording times for recording the image recordings are selected from the ECG-triggered recording times as a function of a heart rate of the patient so that an image rate remains constant with a change of the heart rate.

19. A medical device for determining a plurality of ECG-triggered recording times for a cardiac imaging recording of a patient, comprising:
   a medical imaging device that records a plurality of images of a heart of the patient; and
   a control device that:
      assigns the images to specific cardiac phase times,
      compares the images for determining a similarity measure,
      identifies a group of images having the similarity measure, and
      specifies the cardiac phase times associated with the images in the group as the ECG-triggered recording times to be used in the cardiac imaging recording.

* * * * *